(12) United States Patent
Bourquin et al.

(10) Patent No.: US 11,547,865 B2
(45) Date of Patent: Jan. 10, 2023

(54) COLD PLASMA DEVICE FOR TREATING SKIN

(71) Applicant: KONINKLIJKE PHILIPS N.V., Eindhoven (NL)

(72) Inventors: Yannyk Parulian Julian Bourquin, Eindhoven (NL); Achim Hilgers, Eindhoven (NL); Roland Cornelis Martinus Vulders, Eindhoven (NL); Lili-Marjan Brockhuis, Eindhoven (NL); Frank Anton Van Abeelen, Eindhoven (NL); Eduard Gerard Marie Pelssers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1144 days.

(21) Appl. No.: 16/086,502

(22) PCT Filed: Mar. 16, 2017

(86) PCT No.: PCT/EP2017/056188
§ 371 (c)(1),
(2) Date: Sep. 19, 2018

(87) PCT Pub. No.: WO2017/162505
PCT Pub. Date: Sep. 28, 2017

(65) Prior Publication Data
US 2019/0105506 A1   Apr. 11, 2019

(30) Foreign Application Priority Data
Mar. 22, 2016   (EP) ..................... 16161755

(51) Int. Cl.
*A61N 1/44*     (2006.01)
*H05H 1/24*    (2006.01)
(Continued)

(52) U.S. Cl.
CPC .............. *A61N 1/44* (2013.01); *A61N 5/0624* (2013.01); *H05H 1/2406* (2013.01);
(Continued)

(58) Field of Classification Search
CPC ....... A61N 1/44; A61N 5/0624; H05H 1/2406
See application file for complete search history.

(56) References Cited

U.S. PATENT DOCUMENTS 7,113,821 B1 * 9/2006 Sun .................... A61B 5/14514
606/29
8,267,884 B1    9/2012 Hicks
(Continued)

FOREIGN PATENT DOCUMENTS

GB          2454461 B     5/2009
JP          3155121 U     11/2009
(Continued)

OTHER PUBLICATIONS

"Y.-F. Li et all, In vivo skin treatment using two portable plasma devices: Comparison of a direct and indirect cold atmospheric plasma treatment, Clinical Plasma Medicine (2013)".

*Primary Examiner* — Kevin Joyner

(57) ABSTRACT

The present application relates to a cold plasma device (1) for treating skin (5). The cold plasma device (1) comprises a cold plasma generator (3) adapted to generate cold plasma that produces reactive species for treating said skin (5), and a manipulator (10) adapted to manipulate said skin (5) to increase exposure of bacteria on said skin to said reactive species during use of the device.

20 Claims, 12 Drawing Sheets

(51) Int. Cl.
 *A61N 5/06* (2006.01)
 *A61L 2/00* (2006.01)
 *A61L 2/14* (2006.01)
 *A61B 18/00* (2006.01)
(52) U.S. Cl.
 CPC ... *A61B 2018/00583* (2013.01); *A61L 2/0011* (2013.01); *A61L 2/14* (2013.01); *A61L 2202/11* (2013.01); *H05H 2245/30* (2021.05)

(56) References Cited

U.S. PATENT DOCUMENTS

| | | |
|---|---|---|
| 2012/0259270 A1 | 10/2012 | Wandke |
| 2013/0064726 A1* | 3/2013 | Morfill ..................... A61L 2/14 |
| | | 422/186.21 |
| 2013/0310731 A1 | 11/2013 | Gutsol |
| 2014/0128780 A1 | 5/2014 | Kennedy |
| 2014/0147333 A1 | 5/2014 | Morfill |
| 2014/0200506 A1 | 7/2014 | Zemel |
| 2015/0133903 A1 | 5/2015 | Moeskops |
| 2016/0136062 A1 | 5/2016 | Woodland |
| 2017/0216615 A1 | 8/2017 | Pledge |

FOREIGN PATENT DOCUMENTS

| | | |
|---|---|---|
| JP | 2010246868 | 11/2010 |
| WO | 2015071099 A1 | 5/2015 |
| WO | 2015165986 A1 | 11/2015 |

* cited by examiner

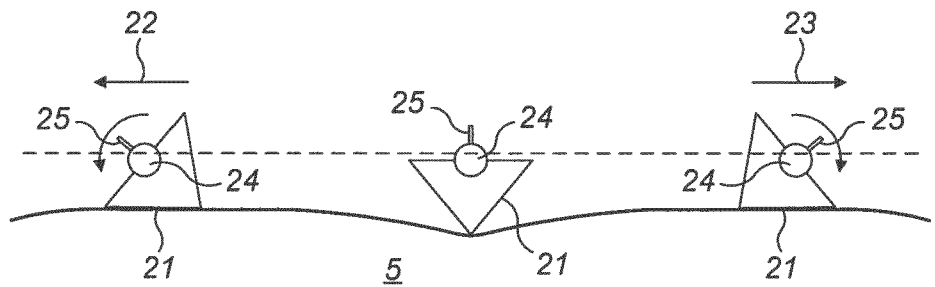
FIG. 8
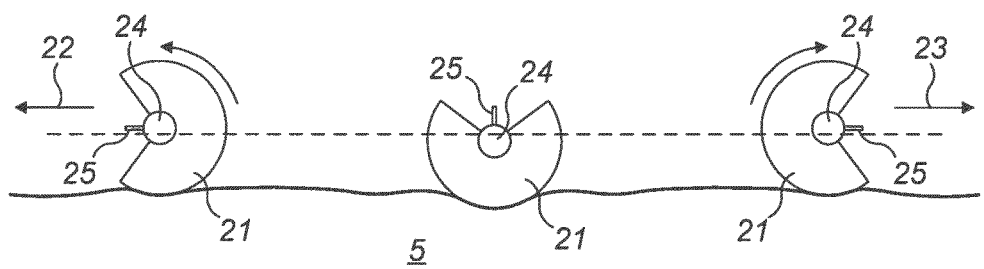
FIG. 9
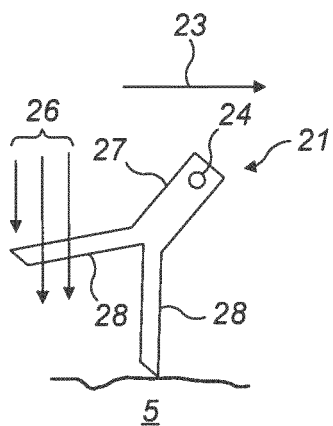 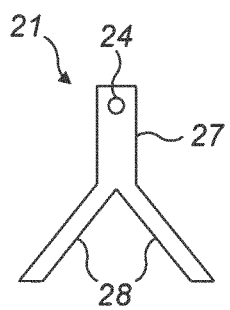 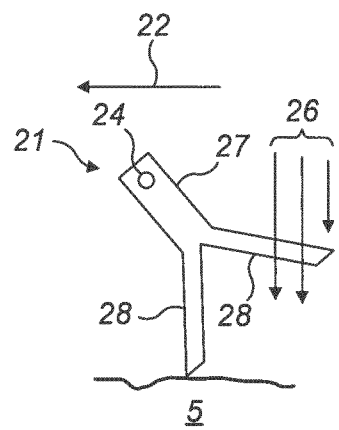
FIG. 10a      FIG. 10b      FIG. 10c ated by reference herein.
COLD PLASMA DEVICE FOR TREATING SKIN This application is the U.S. National Phase application under 35 U.S.C. § 371 of International Application No. PCT/EP2017/056188, filed on Mar. 16, 2017, which claims the benefit of International Application No. 16161755.0 filed on Mar. 22, 2016. These applications are hereby incorporated by reference herein.

FIELD OF THE INVENTION

This disclosure relates to a cold plasma device for treating skin.

BACKGROUND OF THE INVENTION

It is known to use a cold plasma device to disinfect objects. A cold atmospheric plasma generates reactive species, such as oxygen and nitrogen species, that are biologically active and able to inactivate bacteria.

US2013/310731 discloses a method and device for non-thermal plasma treatment of human tissue in which method a current through the both the plasma and the tissue is employed to maintain the plasma proximate to the tissue being treated.

US2014/200506 discloses method and device for treating a nail fungal infection by providing an electrode adapted to be place proximate to the area of interest and applying an electrical field and a plasma to the area of interest.

US2012/0259270 discloses a cold plasma device that includes a flexible electrode and dielectric assembly that can adapt to the shape of the surface being treated. When the device is being used on skin, the flexibility of the electrode and dielectric will create an even spacing between the dielectric and the skin.

Flexible surfaces often have inaccessible areas caused by features of the surface (for example folds or crevices), and so the reactive species may not be able to reach into these areas, even if the shape of the cold plasma device is adapted to the shape of the surface. Skin typically has inherent cavities, for example hair follicles, sebaceous glands, sweat glands, wrinkles, and cavities formed underneath layers of corneocytes. Bacteria can be present in these cavities and the reactive species of the cold plasma may not be able to penetrate into the cavities.

SUMMARY OF THE INVENTION

It is an object of the invention to provide a cold plasma device for treating skin which substantially alleviates or overcomes one or more of the problems mentioned above.

The invention is defined by the independent claims. The dependent claims define advantageous embodiments.

According to a first aspect of the present invention, there is provided a cold plasma device for treating skin, the cold plasma device comprising:

a cold plasma generator adapted to generate cold plasma that produces reactive species for treating said skin, and a manipulator adapted to manipulate said skin to increase exposure of bacteria on said skin to said reactive species during use of the device.

The manipulator may pull, stretch, rub, brush or otherwise manipulate the skin which will increase the exposure of bacteria on the skin to the reactive species. For example, the manipulator ensures that wrinkles are smoothed out and the skin is stretched such that the reactive species can penetrate into the cavities of the skin. A stretching action will also increase exposure of bacteria between corneocyte layers to the reactive species. Moreover, manipulation of the skin may result in bacteria on the skin and/or hair being exposed to more of the reactive species. For example, brushing may move bacteria from hidden locations (e.g. within hair follicles) such that they are exposed to the reactive species. In addition, manipulation may move hairs on the skin so that bacteria underneath the hairs are exposed to the reactive species.

The manipulator may comprise a movable member arranged to contact said skin during use of the cold plasma device.

The movable member may be pivotally mounted to the cold plasma device.

The movable member provides for stretching or otherwise manipulating the skin. By contacting the skin the movable member also provides a rubbing or scraping action as the device is moved across the skin, which may also help to expose more of the bacteria on the skin to the reactive species of the cold plasma.

The cold plasma device may further comprise an actuator adapted to move the movable member relative to the remainder of the device.

The actuator causes further movement of the movable member, which may provide better manipulation of the skin, or it may provide manipulation without having to move the device across the skin manually. Furthermore, use of an actuator can ensure that the movable member manipulates the skin in a controlled manner.

In one example, the actuator may be adapted to rotate the movable member relative to the remainder of the device. Such rotation can stretch the skin in multiple directions, as well as providing a brushing or scraping action that may increase exposure of bacteria on the skin to the reactive species.

Alternatively or additionally, the actuator may be adapted to alternate the direction of movement of the movable member relative to the remainder of the device. Alternating the direction of movement will increase the manipulation, particularly stretching and rubbing, thus increasing exposure of bacteria on the skin to the reactive species.

In another example, the actuator may be adapted to cause the movable member to vibrate relative to the remainder of the device. Such vibration will have a similar effect to the rotation described above—it will increase manipulation and therefore increase exposure of bacteria on the skin to the reactive species.

The manipulator may comprise a stretcher member. Stretching the skin will cause wrinkles and folds to be flattened out, and may cause cavities in the skin to be exposed, thus exposing more bacteria on the skin to the reactive species of the cold plasma. In addition, a stretcher member may lift and move hairs such that bacteria underneath the hairs are exposed to the reactive species.

In one example, the stretcher member may be elongate. The elongate stretcher member may extend in a direction substantially perpendicular to a direction in which the device is moved across the skin during use of the device. In this way, the stretcher member may act to scrape or rub the skin as well as stretching it, all of which increase exposure of bacteria on the skin to the reactive species.

The stretcher member may be pivotally mounted to the device.

A pivotally mounted stretcher member may pivot in different directions depending on the direction in which the device is being moved across the skin. Therefore, the stretcher member can effectively manipulate the skin.

In some examples, the rotation of the stretcher member may be limited by a stop. The stop may be arranged such that when the stretcher member is against the stop at least a part of the stretcher member is exposed to the reactive species, and that part of the stretcher member is thereby sterilised.

In other examples, the rotation of the stretcher member may be limited in two directions by at least one stop. The at least one stop may be arranged such that when the stretcher member is in a maximum rotated position, either way, at least a part of the stretcher member is exposed to the reactive species. In this way, both sides of the stretcher member are sterilised as the device is moved back and forth across the skin and the stretcher member pivots back and forth.

The manipulator may comprise a plurality of stretcher members arranged in adjacent lines.

By arranging the stretcher members in adjacent lines a region of the skin between the stretcher members is individually stretched during use of the device, thereby increasing exposure of bacteria on the skin to the reactive species of the cold plasma.

In some examples, the distance between the stretcher members may be greater than the length of the stretcher members themselves, such that the stretcher members are not able to overlap and block movement of the reactive species to said skin.

In other examples, the manipulator may comprise a plurality of stretcher members arranged in a line. Therefore, the individual stretcher members can adapt to variations in the skin across the width of the device.

The cold plasma device may further comprise an actuator adapted to rotate the stretcher member. The actuator causes further movement of the stretcher member, which may provide better manipulation of the skin, or it may provide manipulation without having to move the device across the skin manually. Furthermore, use of an actuator can ensure that the stretcher member manipulates the skin in a controlled manner.

The manipulator may comprise two or more stretcher members, and the device may further comprise an actuator that is adapted to rotate adjacent stretcher members in opposite directions such that a region of said skin between the two stretcher members is stretched. Therefore, there is an increased stretching action on the region of the skin between the two stretcher members, which increases exposure of bacteria on the skin to the reactive species of the cold plasma.

The stretcher member may have a triangular cross-section, with a point of the triangular cross-section being adapted to contact the skin. A triangular cross-section will provide a scraping and pulling action on the skin. Alternatively, the stretcher member may have a cylindrical or partly cylindrical cross-section. A cylindrical or partly cylindrical cross-section may provide less aggressive manipulation of the skin.

A part of the stretcher member may have a high-friction surface. Such a high friction surface will increase the manipulation of the skin, for example the stretching and rubbing actions.

Alternatively or additionally, the stretcher member or members may include protrusions. For examples, the stretcher member may include resiliently deformable protrusions such as bristles or groups of bristles. Such bristles will provide a brushing action on the skin, which may provide the manipulation by moving or removing some parts of the skin and/or hair to expose bacteria to the reactive species. Also, a brushing action may be less aggressive than other forms of manipulation.

In addition, during use resiliently deformable protrusions will themselves be exposed to the reactive species as the protrusions deform one way and then another. Therefore, such resiliently deformable protrusions will be sterilised during use of the device.

The manipulator may be cylindrical and may be adapted to be rolled across said skin. In this way, the skin can still be manipulated to increase exposure of bacteria on the skin to the reactive species of the cold plasma, but rolling may be less aggressive on the skin. This arrangement may cause less irritation.

A cylindrical mesh may form the cylindrical manipulator, and the cold plasma generator may be housed within the cylindrical mesh. Therefore, the cold plasma generator is always proximate to the skin as the cylindrical manipulator is rolled across the skin. The cylindrical mesh allows the reactive species of the cold plasma to exit the cylindrical manipulator and reach the skin.

Alternatively, the cylindrical manipulator may comprise a cylindrical member, within which the cold plasma generator is housed, and the cylindrical manipulator may have one or more openings to allow the reactive species of the cold plasma to exit the cylindrical manipulator and reach the skin.

The cylindrical manipulator may comprise a plurality of protrusions on its peripheral surface. The protrusions may be flexible, for example the protrusions may be resiliently deformable protrusions, such as bristles or groups of bristles. The protrusions may be arranged in groups or lines. Such protrusions increase the manipulation of the skin as the cylindrical manipulator is rolled across the surface, thereby increasing exposure of bacteria on the skin to the reactive species of the cold plasma.

Alternatively, the manipulator may be spherical and may be adapted to be rolled across said skin. Such an arrangement provides similar benefits to the cylindrical manipulator described above. However, additionally, a spherical manipulator can more easily change direction as it is rolled across the skin, giving the user more control during use.

A spherical mesh may form the spherical manipulator, and the cold plasma generator may be housed within the spherical mesh. In this way, the cold plasma generator is always proximate to the skin as the spherical manipulator is rolled across the skin.

Alternatively, the spherical manipulator may comprise a spherical member, within which the cold plasma generator is housed, and the spherical member may comprise one or more openings to allow the reactive species of the cold plasma to exit the spherical manipulator and reach the skin.

The spherical manipulator may comprise a plurality of protrusions on its peripheral surface. The protrusions may be flexible, for example the protrusions may be bristles or groups of bristles. Such protrusions increase the manipulation of the skin as the spherical manipulator is rolled across the surface, thereby increasing exposure of bacteria on the skin to the reactive species of the cold plasma.

In another embodiment, the manipulator may comprise a belt adapted to contact the skin and being mounted on at least two pulleys or rollers, and an actuator may be adapted to rotate the belt. The manipulator may comprise a plurality of such belts. The belts may be parallel to each other. Adjacent belts may be driven in opposite directions of rotation. Such arrangements provide a stretching action on the skin, increasing exposure of bacteria on the skin to the reactive species of the cold plasma.

The at least one belt may comprise a plurality of protrusions on its outer surface. The protrusions may be flexible, for example the protrusions may be bristles or groups or bristles. The at least one belt may include an opening to allow the reactive species of the cold plasma to pass through and reach the skin.

The at least one belt may be adapted such that during use one part of the belt is in contact with said skin and another part of the belt is exposed to the reactive species of said cold plasma. In this way, the belt is sterilised by the reactive species during use of the device.

The manipulator may comprise a fixed member arranged to contact said skin during use of the device.

Such a fixed member will provide a stretching and scraping action as the device is moved across the skin, thereby increasing exposure of bacteria on the skin to the reactive species of the cold plasma.

In some examples, the fixed member may comprise a plurality of protrusions on its outer surface. The protrusions may be flexible, for example the protrusions may be bristles or groups or bristles.

In some examples, the fixed member may comprise a high-friction surface, to increase grip between the fixed member and the skin and thereby increase manipulation.

In some examples, the manipulator may comprise a mesh.

A mesh permits the reactive species of the cold plasma to easily pass from one side to the other, via openings in the mesh. In this way, reactive species can pass from the cold plasma device to the skin via the mesh, while at the same time the mesh acts to manipulate the skin to increase exposure of bacteria on the skin to the reactive species of the cold plasma.

In one embodiment, the mesh may comprise a part of the cold plasma generator, for example the mesh may be an electrode or the mesh may be a dielectric component of the cold plasma generator. In this way, the cold plasma and the reactive species are generated in the immediate vicinity of the skin, providing effective treatment to the skin.

The manipulator may comprise a plurality of protrusions adapted to contact said skin during use of the device. Such protrusions can manipulate the skin by pulling, pushing, brushing and scraping.

The protrusions may be flexible. The protrusions may be resiliently deformable. The protrusions may be bristles. Multiple bristles may be grouped to form at least one brush. Such protrusions may be applied to any part of any of the manipulator.

The manipulator may comprise a resiliently flexible material. That is, any part of the manipulator may comprise a resiliently flexible material.

Different parts of a resiliently flexible manipulator will be exposed to the reactive species as the manipulator deforms one way and then another during use of the device. Therefore, such a resiliently flexible manipulator will be sterilised during use of the device.

In various examples, the whole or a part of the manipulator may comprise a resiliently deformable material. In one example, only protrusions that protrude from a surface of the manipulator are resiliently flexible. In other examples, the entire manipulator may be resiliently flexible.

By making at least a part of the manipulator from a resiliently flexible material the manipulator may be able to adapt to the shape of the skin being treated, thereby providing manipulation across a larger part of the skin. By increasing the contact area between the manipulator and the skin the skin can be manipulated more.

The cold plasma generator and the manipulator may be integrally formed, with the manipulator being disposed on a surface of the cold plasma generator. In this way, the cold plasma and the reactive species are generated in the immediate vicinity of the skin, providing effective treatment to the skin.

In one example, the cold plasma generator may comprise a first electrode and a second electrode that are embedded within a dielectric material, and a surface of the dielectric material may comprise the manipulator. The surface of the dielectric material that comprises the manipulator may be profiled, for example it may comprise a plurality of protrusions.

The second electrode may be disposed between the first electrode and the surface of the dielectric material that comprises the manipulator, and the second electrode may comprise openings to permit reactive species of said cold plasma filaments to reach said skin during use. In this example, the second electrode may comprise a mesh.

In one example, the second electrode may be configured to provide a substantially even distance between the second electrode and the surface of the dielectric material that comprises the manipulator. In this case, the second electrode may be shaped to match the profile of the surface of the dielectric material that comprises the manipulator.

In another example, the first electrode and the second electrode may be equally spaced from the surface of the dielectric material that comprises the manipulator. For example, the first and second electrodes may be embedded within the dielectric material and be arranged side-to-side and interwoven. In this case, the first electrode and the second electrode may be shaped to match the profile of the surface of the dielectric material that comprises the manipulator so that there is a substantially even distance between each of the first and second electrodes and the profiled surface of the dielectric material.

According to a further aspect of the invention, there is provided a kit comprising a cold plasma device for treating skin and a manipulator device comprising a manipulator adapted to manipulate said skin to increase exposure of bacteria on said skin to said reactive species during use of the device.

In this example, a user can use the manipulator device to prepare the skin, before using the cold plasma device to treat the skin.

The cold plasma device may include any of the features described above in relation to the cold plasma generator. Similarly, the manipulator device may include any of the features of the manipulator described above.

In the above examples, the cold plasma device is suitable for treating skin. For example, the cold plasma device may be a deodorising device for use on skin, in particular to inactivate bacteria on the skin.

The cold plasma device may also be suitable for treating other flexible surfaces. For example the cold plasma device may be used for disinfecting apparatus, for example toothbrushes, shavers, catheters.

In other examples, the cold plasma device may be suitable for treating wounds or other damage to skin or flesh, for example to reduce infection.

In further examples, the cold plasma device may be suitable for treating flexible surfaces, for example bed sheets, curtains, shoes, or plastic coverings.

In other examples, the cold plasma device may also be suitable for treating non-flexible surfaces where some manipulation is beneficial in increasing exposure of bacteria on the non-flexible surface to the reactive species of the cold plasma. For example, the cold plasma device could be used to treat teeth, and in this case the manipulator will act to move or scrape away bio films on the surface of the teeth such that the reactive species can reach the teeth themselves.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which:

FIG. 2b shows an exploded view of the cold plasma device of FIG. 2a;

FIG. 4b shows an enlarged view of a part of the manipulator of the cold plasma device of FIG. 4a;

FIG. 5b shows an enlarged view of a part of the manipulator of the cold plasma device of FIG. 5a;

FIG. 8 shows a schematic diagram of an example stretcher member;

FIG. 9 shows a schematic diagram of another example stretcher member;

FIGS. 10a to 10c show schematic diagrams of example rotatable stretcher members;

DETAILED DESCRIPTION OF THE EMBODIMENTS

Figure 1:
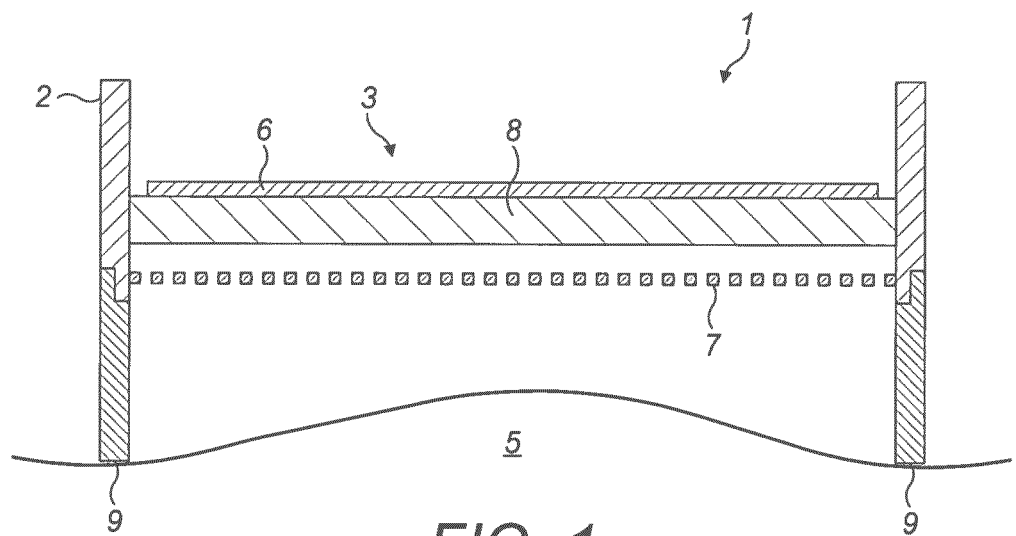
FIG. 1 shows an example cold plasma device for treating skin.

The example cold plasma device 1 shown in FIG. 1 comprises a housing 2 that holds a cold plasma generator 3.

The term cold plasma is used to describe plasmas at an ion temperature that is less than about 100 degrees Celsius, and is therefore suitable for use on and around people, particularly for treating skin.

The cold plasma generator 3 of the example of FIG. 1 comprises a first electrode 6, a second electrode 7, and a dielectric material 8 disposed between the first and second electrodes 6, 7. As shown in FIG. 1, the cold plasma generator 3 extends across the housing 2 so that it is substantially parallel with an end face 9 of the housing 2. In this way, the cold plasma generator 3, particularly the second electrode 7 (which is closer to the skin 5), is substantially evenly spaced from the skin 5 during use.

The cold plasma generator 3 is connected to a power supply (not shown) within the device 1 such that a voltage is generated across the first and second electrodes 6, 7. The dielectric material 8 acts to electrically insulate the first electrode 6 from the second electrode 7.

The above-described structure of the cold plasma generator 3 is termed a dielectric barrier discharge cold plasma generator. A pulsating direct current, or alternating voltage, with amplitude of several kilovolts is applied across the first electrode 6 and the second electrode 7. The dielectric material 8 prevents direct discharge between the first electrode 6 and the second electrode 7. Instead, filaments (micro-discharges) are generated between the dielectric material 8 and the second electrode 7. These filaments are created by the ionisation of molecules present between the first and second electrodes 6, 7, for example nitrogen molecules within the air, caused by the high voltage. This ionisation process releases electrons which collide with, and ionise, other molecules, such as radicals, present between the first and second electrodes 6, 7. These further molecules may collide with other molecules, resulting in a cascading effect generating the reactive species.

In this way, reactive species are generated from the air between the second electrode 7 and the dielectric material 8. Amongst others, the reactive species may include nitrogen oxides, atomic oxygen, Ozone, hydroxyl, reactive oxygen species, reactive nitrogen species, and free electrons. The reactive species may be charged (e.g. ions or free electrons) or non-charged. These reactive species are chemically reactive and can inactivate bacteria, and are thus useful for treating surfaces such as skin.

The ion temperature of the cold plasma is the temperature of the ions and the neutral molecules after being thermalized, i.e. once they have reached thermal equilibrium. In the treatment of skin, the temperature rise may be limited to a few degrees Celsius above ambient temperature. However, for treating other surfaces a higher voltage can be used to generate a higher temperature above ambient temperature, for example up to 100 degrees Celsius.

The skilled person will appreciate that the cold plasma generator 3 may have an alternative structure. For example, US20140147333 describes two alternative arrangements of cold plasma generators. A first example is a surface micro discharge cold plasma generator in which the dielectric material fills the entire space between the first and second electrodes. Another example is a self-sterilizing surface cold plasma generator, in which the first and second electrodes are embedded in dielectric material, and so the filaments are emitted from a surface of the dielectric material.

Moreover, the skilled person will appreciate that cold plasma can be generated within a gas that is not air. For example, other gasses can be provided to the space between the dielectric material and the second electrode, and these gasses would be ionised by the cold plasma generator and create reactive species. Such other gasses could be provided from a compressed gas source. For example, a cold plasma can be generated from a mixture of Argon gas and Oxygen. It is possible to control the type and quantity of reactive species generated by selecting different gasses.

Figure 2A:
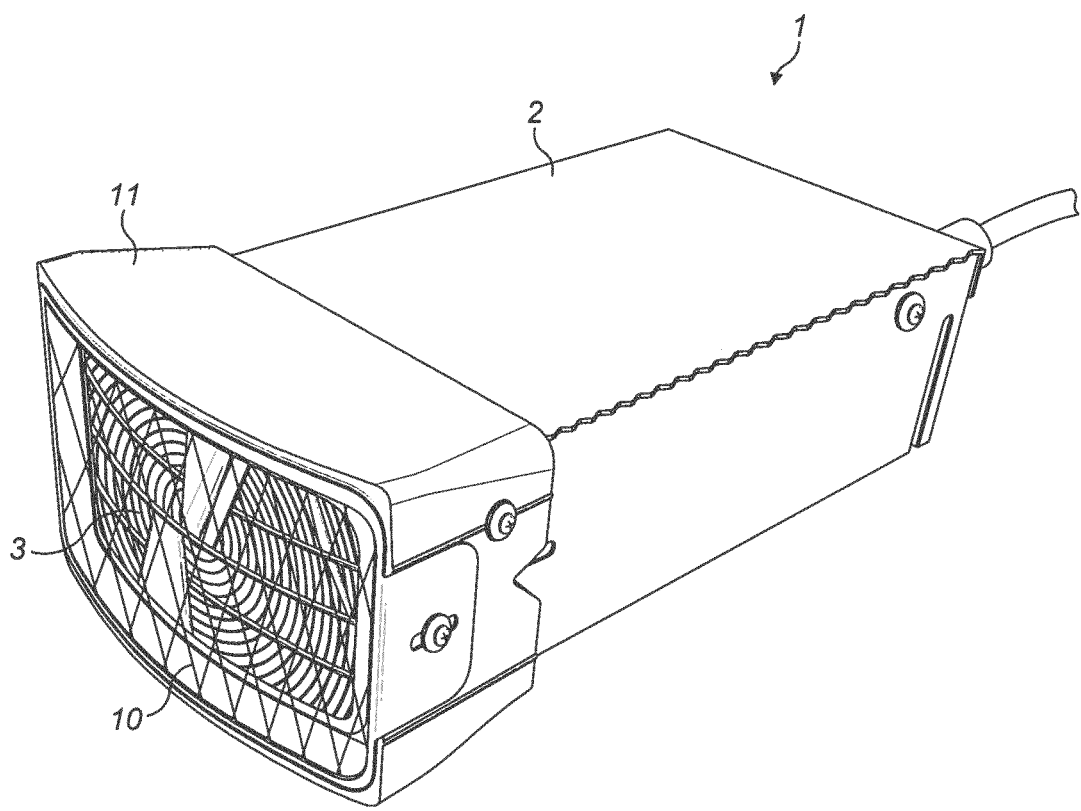
FIG. 2a shows a perspective view of an example cold plasma device for treating skin.
Figure 2B:
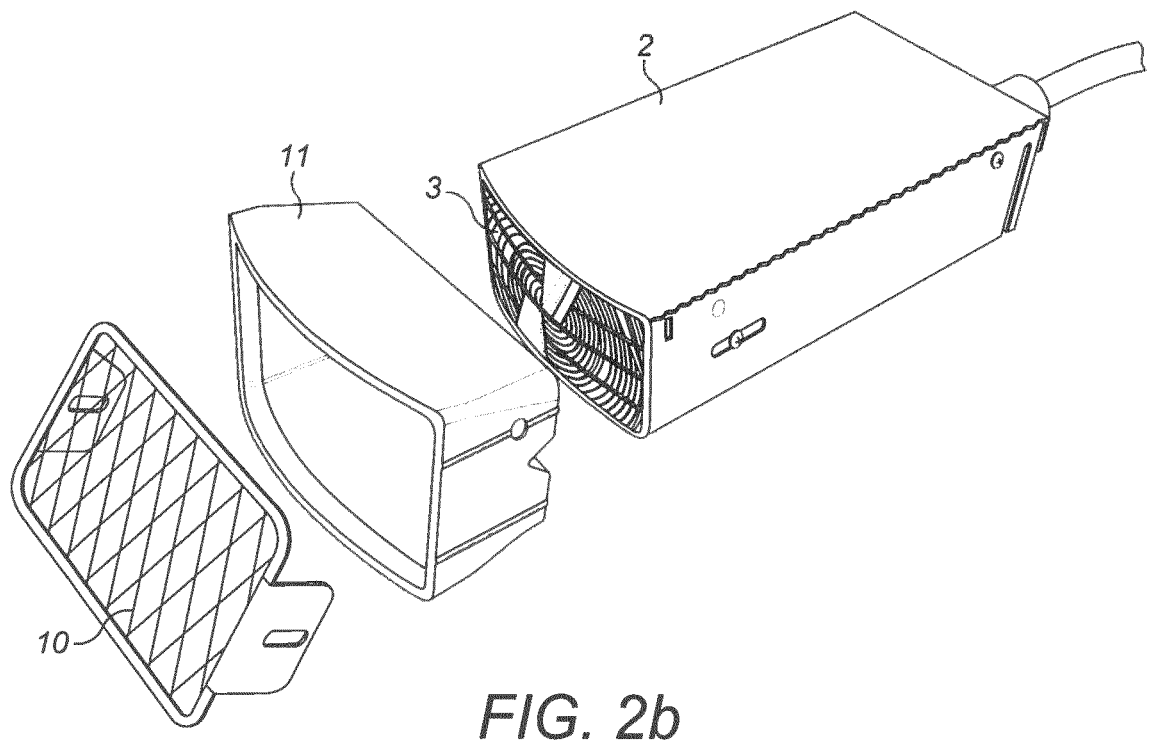

The cold plasma device 1 of FIG. 2a and FIG. 2b comprises a housing 2 that houses a cold plasma generator 3, a power supply (not shown) and other components of the device 1.

The power supply may comprise a replaceable battery, a rechargeable battery, or a connection to an external power source (e.g. mains electricity). The power source may include other appropriate electrical components (e.g. transformer) to provide suitable electrical power to the cold plasma generator 3.

In addition, the device 1 of FIG. 2a and FIG. 2b comprises a manipulator 10 adapted to manipulate the skin (5, see FIG. 1) to increase exposure of bacteria on the skin (5, see FIG. 1) to reactive species generated by the cold plasma generator 3 during use of the device 1.

As shown in FIG. 2a and FIG. 2b, the device 1 includes a support 11 for the manipulator 10. The manipulator 10 is mounted within the support 11 and the support 11 is attached to the housing 2. Alternatively, the manipulator may be mounted directly to the housing 2.

In some examples, the support 11 and manipulator 10 may be removable from the device 1 so that a user is able to select different attachments for different uses of the device 1. For examples, people have different sized armpits, and so various sized supports 11 could be supplied to allow the device 1 to be used by different people or used for a different area of skin.

Figure 3:
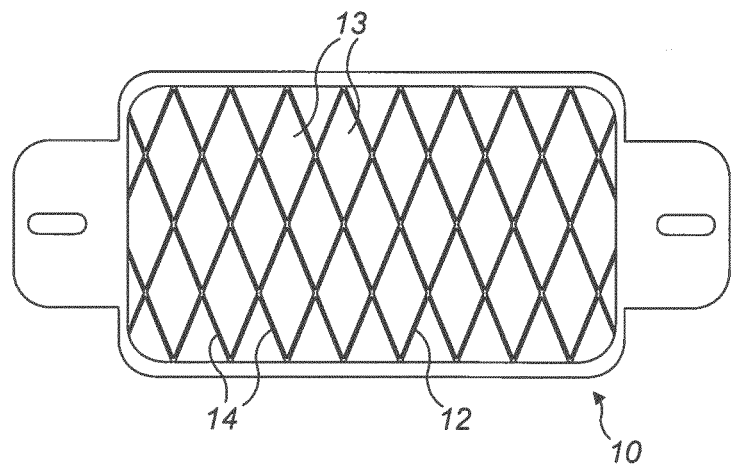
FIG. 3 shows the manipulator of the cold plasma device of FIG. 2a and FIG. 2b.

As shown in FIG. 3, the manipulator 10 of this example comprises a mesh 12. The mesh 12 comprises a series of struts 14 that define a plurality of openings 13 through which the reactive species of the cold plasma can travel to reach the skin (5, see FIG. 1) during use of the device 1.

When the device 1 is in use the manipulator 10 is placed against the skin (5, see FIG. 1) and moved across the skin (5, see FIG. 1), while at the same time the cold plasma generator 3 generates the reactive species for treating the skin (5, see FIG. 1). In addition, the manipulator 10 contacts the skin (5, see FIG. 1) and so defines the minimum spacing between the cold plasma generator 3 and the skin (5, see FIG. 1) during use of the device 1.

As the manipulator 10 is moved across the skin (5, see FIG. 1) it acts to manipulate the skin (5, see FIG. 1) in such a way that bacteria on the skin (5, see FIG. 1) is more exposed to the reactive species of the cold plasma. In particular, the manipulator 10 acts to stretch the skin (5, see FIG. 1) so that folds and wrinkles are leveled out and cavities exposed, while also providing a scraping action that may move or remove parts of the skin to expose cavities or crevices. Such manipulation may also lift or move hairs on the skin, thus exposing bacteria underneath the hairs to the reactive species.

For example, the manipulator 10 acts to stretch and scrape the skin so that cavities defined by hair follicles, sebaceous glands, sweat glands, wrinkles, and even layers of corneocyte, are exposed, resulting in higher exposure of bacteria on the skin to the reactive species.

Figure 4A:
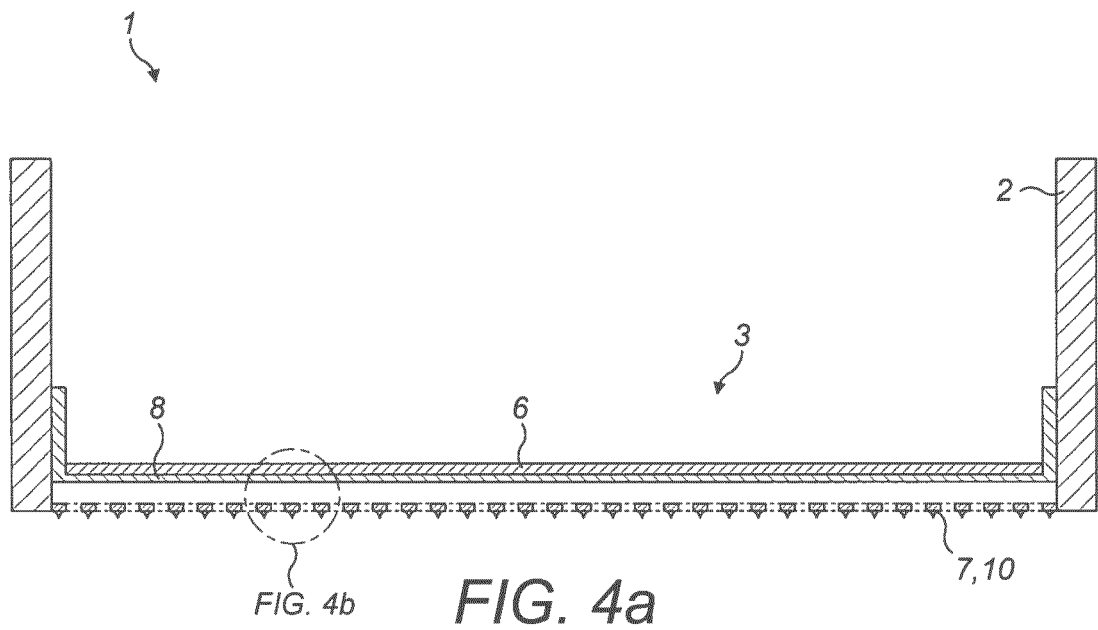
FIG. 4a shows a schematic diagram of an example of a cold plasma device for treating skin.

In the example cold plasma device 1 of FIG. 4a and FIG. 4b, the first electrode 6 and dielectric material 8 of the cold plasma generator are arranged similarly to as explained with reference to FIG. 1. However, in this example the second electrode 7 and the manipulator 10 are part of the same component.

Figure 4B:
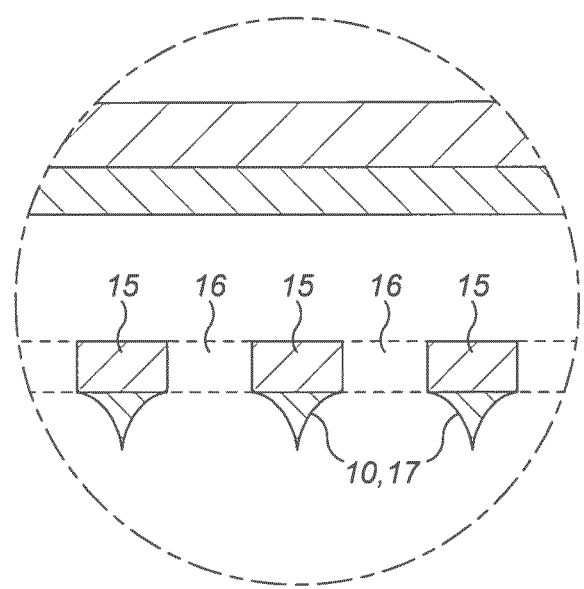

In particular, as shown more clearly in FIG. 4b, the second electrode 7 comprises a mesh with struts 15 that define a plurality of openings 16. Attached to, or integral with, the struts 15 of the second electrode 7 is the manipulator 10. The openings 16 permit the reactive species generated in the space between the dielectric material 8 and the second electrode 7 to reach the skin (5, see FIG. 1).

In this example, the manipulator 10 comprises a plurality of protrusions 17 mounted to the struts 15 of the manipulator 10. The protrusions 17 are pointed such that they engage the skin (5, see FIG. 1) and act to stretch and scrape the skin (5, see FIG. 1) as the cold plasma device 1 is moved across the skin (5, see FIG. 1). The protrusions 17 may be integral with, or attached to, the second electrode 7.

In one example, the protrusions 17 are elongate and extend along the struts 15 of the mesh. In another example, each strut 15 includes a plurality of individual protrusions 17.

The protrusions 17 may be rigid, or they may be resiliently deformable for example made from a rubber material. In some examples, the protrusions 17 may be bristles, or groups of bristles.

Figure 5A:
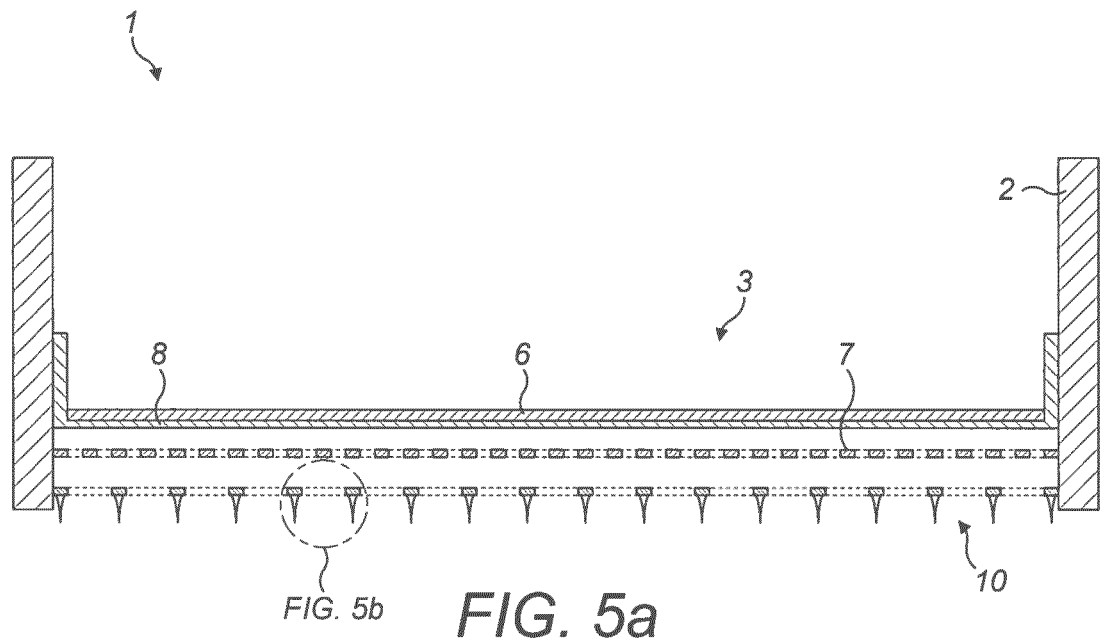
FIG. 5a shows a schematic diagram of an example of a cold plasma device for treating skin.
Figure 5B:
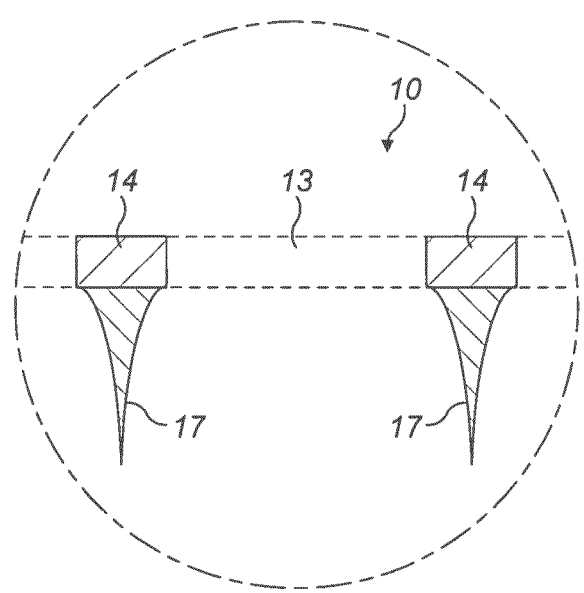

In the example of FIG. 5a and FIG. 5b, the manipulator 10 is separate to, and spaced from, the second electrode 7. In this example, the second electrode 7 comprises a mesh that allows reactive species generated in the space between the dielectric material 8 and the second electrode 7 to reach the skin (5, see FIG. 1) during use.

The manipulator 10 also comprises a mesh, with struts 14 and openings 13 that permit the reactive species to reach the skin (5, see FIG. 1) during use of the device 1. The struts 14 of the manipulator 10 include protrusions 17 that may be attached to, or integral with, the struts 14.

The protrusions 17 are pointed such that they engage the skin (5, see FIG. 1) and act to stretch and scrape the skin (5, see FIG. 1) as the cold plasma device 1 is moved across the skin (5, see FIG. 1).

In one example, the protrusions 17 are elongate and extend along the struts 14 of the mesh. In another example, each strut 14 may include a plurality of individual protrusions 17.

The protrusions 17 may be rigid, or they may be resiliently deformable for example made from a rubber material. In some examples, the protrusions 17 may be bristles, or groups of bristles.

Figure 6A:
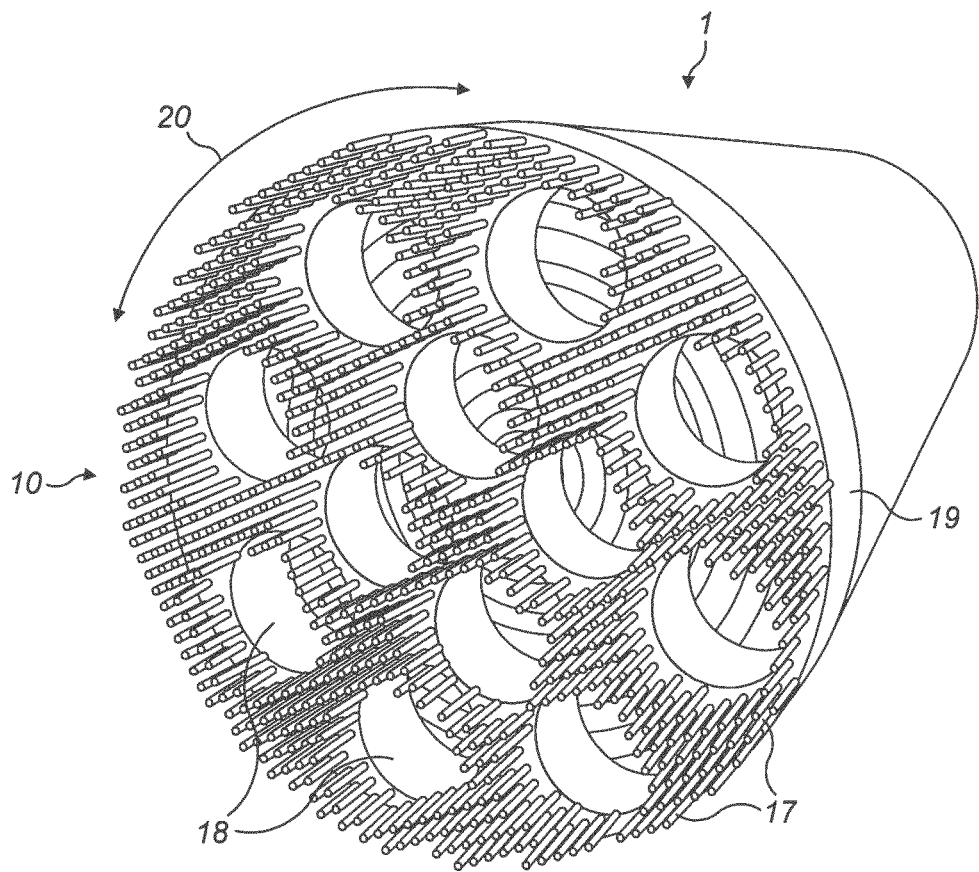
FIGS. 6a to 6c show examples of manipulators for a cold plasma device for treating skin.
Figure 6B:
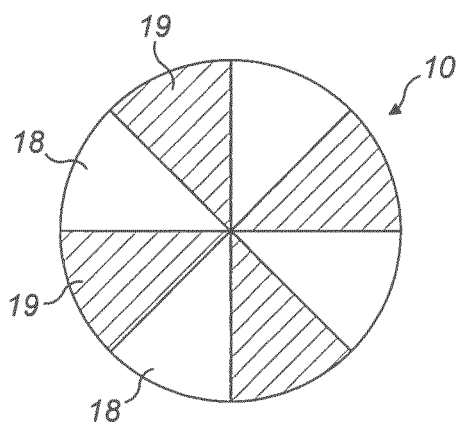
Figure 6C:
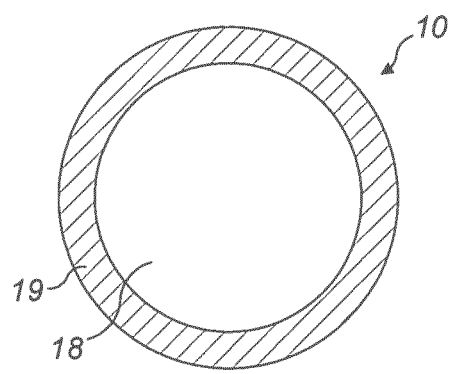

In the examples of FIG. 6a to FIG. 6c the manipulator 10 comprises one or more openings 18.

In the example of FIG. 6a, the manipulator 10 comprises a plate 19 that includes a plurality of openings 18. A plurality of protrusions 17 are disposed on the plate 19. The protrusions 17 may be integral with, or mounted to, the plate 19. The openings permit reactive species of the cold plasma to reach the skin (5, see FIG. 1) during use of the device. In the example of FIG. 6a, the openings 18 are circular and spaced from each other in the plate 19.

In the example of FIG. 6b, the manipulator comprises a plurality of plates 19, each defining a segment of the manipulator 10. Between each plate 19 is an opening 18 to permit reactive species of the cold plasma to reach the skin (5, see FIG. 1) during use of the device. Similarly to the example of FIG. 6a, the plates 19 may comprise a plurality of protrusions that act to manipulate the skin (5, see FIG. 1). The protrusions may be integral with, or mounted to, the plates 19.

In the example of FIG. 6c, the manipulator 10 comprises a ring-shaped plate 19 defining a single, circular opening 18 therein. The plate 19 may comprise a plurality of protrusions that act to manipulate the skin (5, see FIG. 1). The protrusions may be integral with, or mounted to, the plates 19.

It will be appreciated that the manipulator 10 may take a variety of other shapes.

As indicated by arrow 20 in FIG. 6a, the cold plasma device 1 may include an actuator (not shown) adapted to move the manipulator 10 relative to the remainder of the cold plasma device 1.

In this example, the actuator is adapted to rotate the manipulator 10. In particular, the actuator is adapted to alternate the direction of rotation of the manipulator 10. In other examples, the actuator may be adapted to move the manipulator 10 in a linear direction, which may be alternated. In other examples, the actuator may be adapted to vibrate the manipulator 10.

In the example illustrated in FIG. 7a to FIG. 7d, the cold plasma device 1 includes a manipulator 10 that comprises a plurality of stretcher members 21, in this example three stretcher members 21. The stretcher members 21 are adapted to contact the skin (5, see FIG. 1) during use.

Figure 7A:
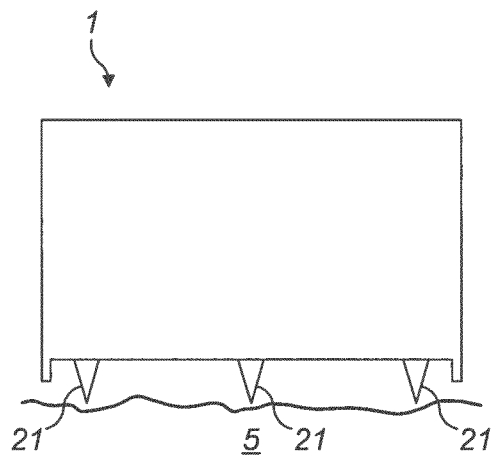
FIGS. 7a to 7d show an example of a cold plasma device for treating skin, the cold plasma device including a manipulator having stretcher members.
Figure 7B:
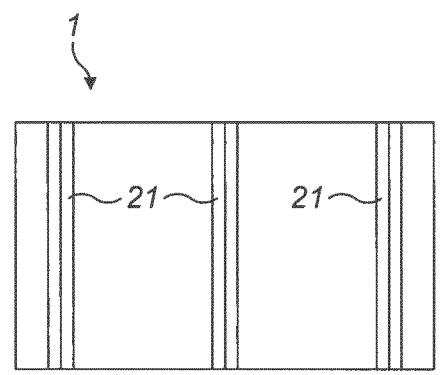

As shown in FIG. 7b, the stretcher members 21 are elongate and extend across the device 1 in parallel to each other. The reactive species of the cold plasma can pass between the stretcher members 21 to reach the skin 5 during use.

Figure 7C:
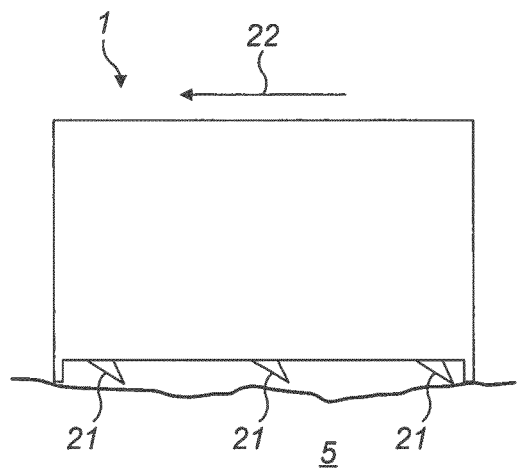
Figure 7D:
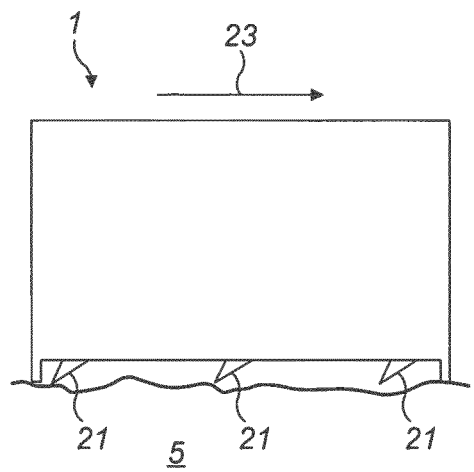

As shown in FIG. 7c and FIG. 7d, when the device 1 is moved in the direction of arrows 22, 23 across the skin 5, the stretcher members are folded back in an opposite direction. In particular, the stretcher members 21 may be pivotally mounted to the manipulator 10. In this case, the stretcher members 21 may comprise a rigid material.

In other examples, the stretcher members 21 may comprise a resiliently deformable material such that they deform during use.

The deforming of the stretcher members 21 causes the skin to be stretched and scraped to provide manipulation and increase exposure of bacteria on the skin 5 to the reactive species of the cold plasma.

FIG. 8 and FIG. 9 show different examples of the stretcher members 21 of FIGS. 7a to 7d.

In particular, FIG. 8 shows stretcher members 21 with a triangular cross-section that is mounted on pivot 24. The stretcher member 21 rotates about pivot 24 as the cold plasma device is moved across the skin 5 in the direction of arrows 22, 23.

In the example of FIG. 9, the stretcher members 21 have a partly cylindrical cross-section and are mounted on a pivot 24. The stretcher member 21 rotates about pivot 24 as the cold plasma device is moved across the skin 5 in the direction of arrows 22, 23.

In both examples of FIG. 8 and FIG. 9, the stretcher members 21 are provided with a stop 25 that limits the rotation of the stretcher members 21 about the pivot 24. In these examples, a single stop 25 is provided per stretcher member that acts to limit the degree of rotation of the stretcher members 21 in both directions. However, it will be appreciated that more than one stop 25 may be provided per stretcher member 21.

When the stretcher members 21 are in a rotated position, as shown in FIG. 8 and FIG. 9, the tops of the stretcher members 21 are exposed to the reactive species of the cold plasma, and are thereby sterilised. Therefore, during use of the device the stretcher members 21 are sterilised so that use of the device does not spread bacteria over the skin 5.

FIG. 10a to FIG. 10c show another example of a stretcher member 21 of FIGS. 7a to 7d.

In this example, the stretcher member 21 comprises a hub portion 27, which is attached to the pivot 24, and two protruding arms 28 that form a 'V-shape' and contact the skin 5. As shown in FIG. 10a and FIG. 10c, the stretcher member 21 rotates as the device is moved across the skin 5 in the direction of arrows 22, 23.

As with previous examples, in the each of the rotated positions shown in FIG. 10a and FIG. 10c, one arm 28 of the stretcher member 21 is exposed to reactive species 26 of the cold plasma, thus sterilising that arm 28. Therefore, during use of the device the stretcher members 21 are sterilised so that use of the device does not spread bacteria over the skin 5.

Figure 11:
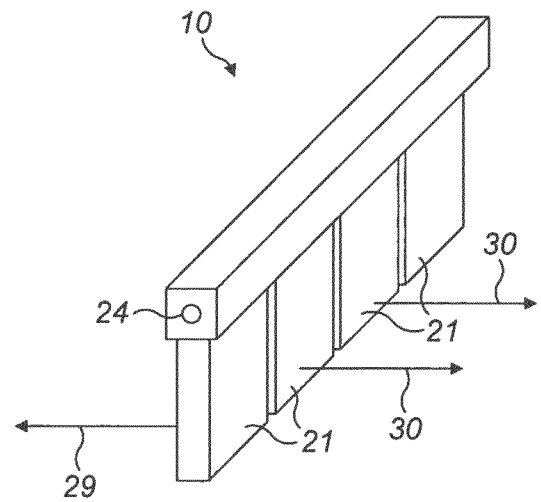
FIG. 11 shows an example of a line of stretcher members.

In the example of FIG. 11, the manipulator 10 includes a plurality of individual stretcher members 21 arranged in a line. The stretcher members 21 are mounted to a pivot 24 and can rotate about the pivot 24 independently of each other. In this way, when the device is moved across the skin the manipulator 10 can adapt to the shape of the skin, taking account of contours. Moreover, if the device were moved such that the manipulator 10 were rotated on the skin, then different stretcher members can pivot in different directions to provide the manipulation, as indicated by arrows 29, 30.

The stretcher members 21 of any of FIG. 7a to FIG. 10c may be arranged as shown in FIG. 11. Furthermore, the manipulator 10 may comprise several of the lines of stretcher members 21 shown in FIG. 11, arranged in parallel as shown in FIG. 7a to FIG. 7d.

Figure 12A:
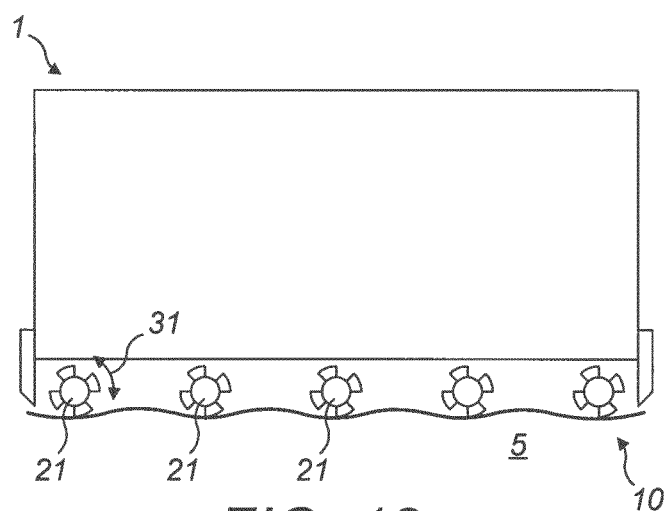
FIG. 12a and FIG. 12b show views of an example cold plasma device for treating skin, having a manipulator comprising cylindrical rollers.
Figure 12B:
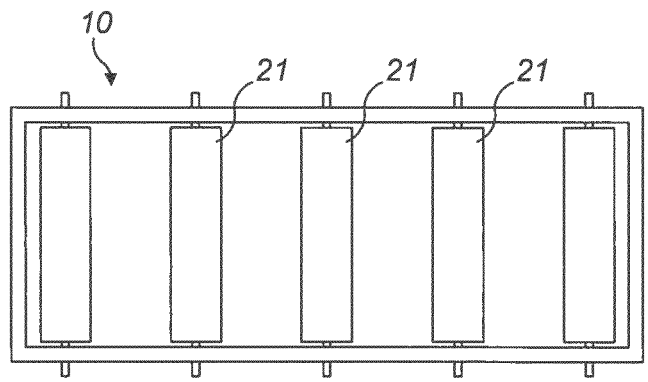

In the example of FIG. 12a and FIG. 12b, the manipulator 10 comprises a plurality of cylindrical stretcher members 21. Each stretcher member 21 is effectively a roller that can be rolled across the skin 5. The stretcher members 21 are arranged in parallel to each other on the manipulator 10.

The roller stretcher members 21 may each have a high friction coating to increase friction between the stretcher members 21 and the skin 5. Additionally or alternatively, the outer surface of the roller stretcher members 21 may be provided with a plurality of protrusions, for example resiliently flexible protrusions or bristles, such that the stretcher members 21 perform a brushing action as well as a stretching action.

As indicated by arrow 31, the cold plasma device 1 may include an actuator adapted to rotate the roller stretcher members 21. Adjacent roller stretcher members 21 may be rotated in opposite directions such that the skin 5 in the region between two roller stretcher members 21 is stretched. The actuator may be adapted to alternate the direction of rotation to increase manipulation.

Figure 13A:
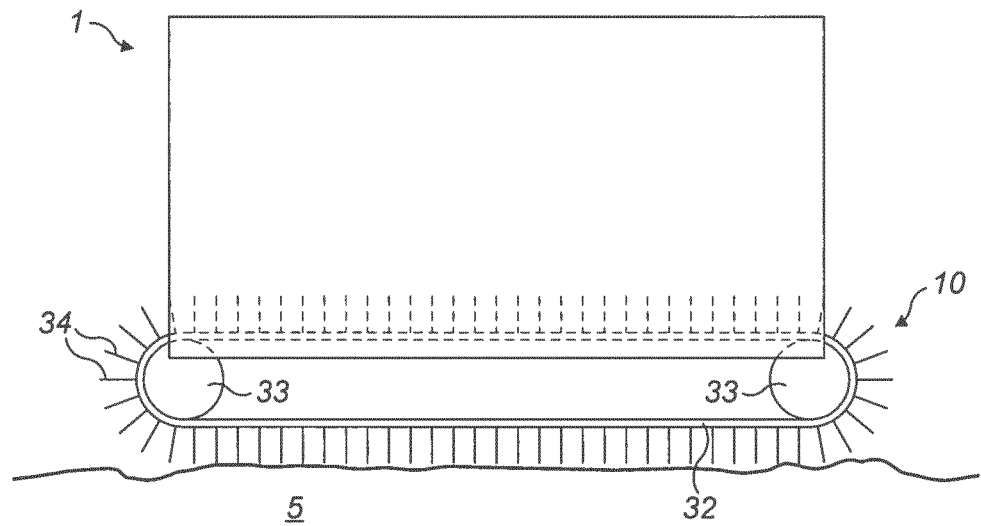
FIGS. 13a to 13c show views of an example cold plasma device for treating skin, having a manipulator comprising belts.
Figure 13B:
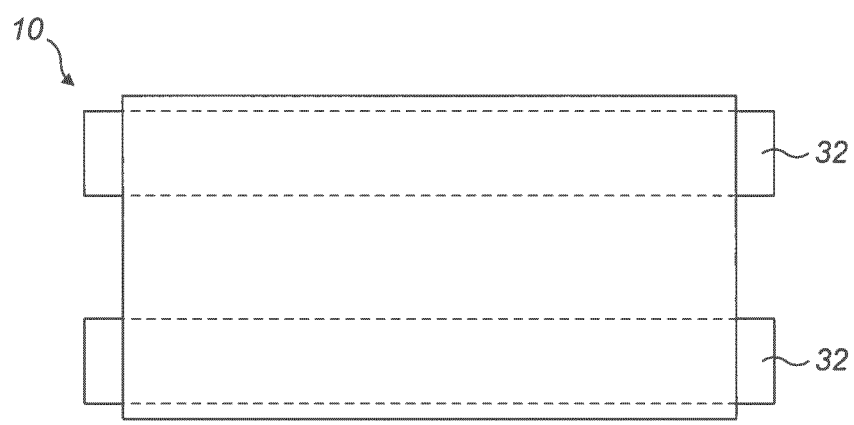
Figure 13C:
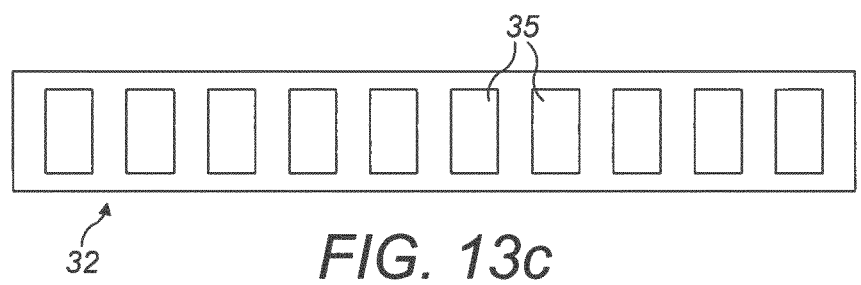

In the example of FIG. 13a to FIG. 13c, the cold plasma device 1 comprises a manipulator 10 in the form of two belts 32, which are mounted on pulleys 33. At least one of the pulleys 33 may be driven by an actuator such that the belts 32 are rotated on the device 1. The belts 32 contact the skin 5 during use of the device 1 and act to manipulate the skin 5 to increase exposure of the reactive species.

As shown in FIG. 13c, the belts 32 may include openings 35 to permit the reactive species of the cold plasma to reach the skin 5.

As shown in FIG. 13a, the belts 32 may include a plurality of protrusions 34 to increase manipulation. The protrusions 34 may be attached to, or integral with, the belts 32. The protrusions may be rigid, or they may be resiliently deformable for example made from a rubber material. In some examples, the protrusions 34 may be bristles, or groups of bristles.

In another example, the device 1 is provided with only one belt 32.

As the belts 32 rotate, during use of the device 1, the tops of the belts 32 are exposed to the reactive species of the cold plasma. In this way, the surfaces of the belts 32 that come into contact with the skin are sterilised during use.

In one example, adjacent belts 32 are rotated in opposite directions to increase manipulation of the skin 5. Alternatively or additionally, the actuator may be adapted to alternate the direction of rotation of the one or more belts 32.

In these examples, the cold plasma device 1 can be moved across the skin in a direction perpendicular to the rotation of the belts 32.

Figure 14A:
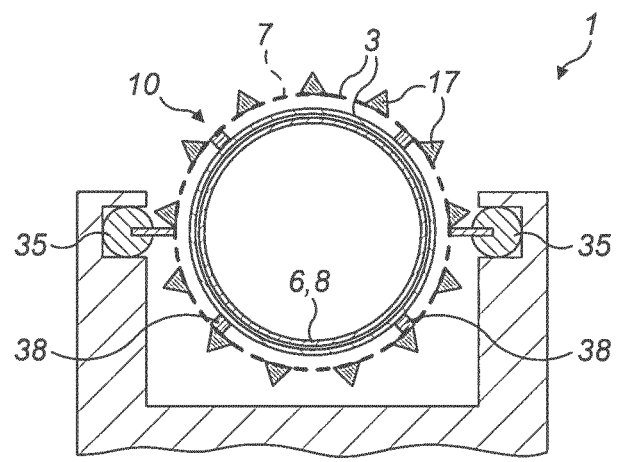
FIG. 14a and FIG. 14b show an example of a cold plasma device for treating skin, having a spherical manipulator.
Figure 14B:
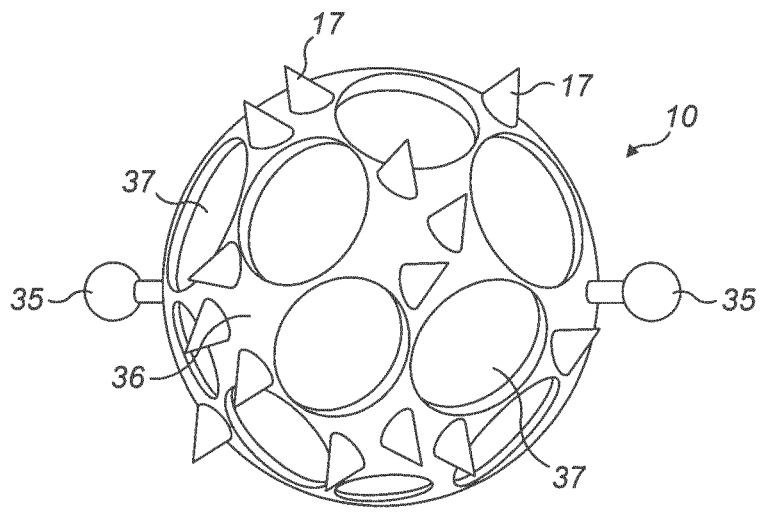

In the example of FIG. 14a and FIG. 14b, the cold plasma device comprises a spherical manipulator 10.

As shown in FIG. 14a, the cold plasma generator 3 is housed within the spherical manipulator 10. In particular, the first electrode 6 and dielectric material 8 are also spherical and located within a spherical second electrode 7. Spacers 38 maintain separation between the second electrode 7 and the dielectric material 8.

In one example, the second electrode 7 comprises a mesh. The mesh may be as described with reference to FIG. 3 to FIG. 5b, and may include protrusions 17 to manipulate the skin. The protrusions 17 may be attached to, or integral with, the spherical mesh 7. The protrusions 17 may be rigid, or they may be resiliently deformable for example made from a rubber material. In some examples, the protrusions 17 may be bristles, or groups of bristles.

Alternatively, the second electrode 7 may be a separate mesh-like component mounted within, and spaced from, a further mesh that forms the manipulator 10.

The spherical manipulator 10 is mounted on pivots 35 that permit the spherical manipulator to be rolled across the skin. The cold plasma generator 3 within the spherical manipulator 10 can be electrically connected to a power source via connections in the pivots 35.

As shown in FIG. 14b, the spherical manipulator 10 may comprise a spherical ball 36 that is provided with a plurality of openings 37. The cold plasma generator (first electrode, second electrode and dielectric material) may be mounted within the spherical ball 36. Alternatively, the spherical ball 36 itself may be the second electrode.

The openings 37 permit the reactive species of the cold plasma to reach the skin during use of the device.

The spherical ball 36 may be provided with protrusions 17. The protrusions 17 may be attached to, or integral with, the spherical ball 36. The protrusions 17 may be rigid, or they may be resiliently deformable for example made from a rubber material. In some examples, the protrusions 17 may be bristles, or groups of bristles.

Figure 15:
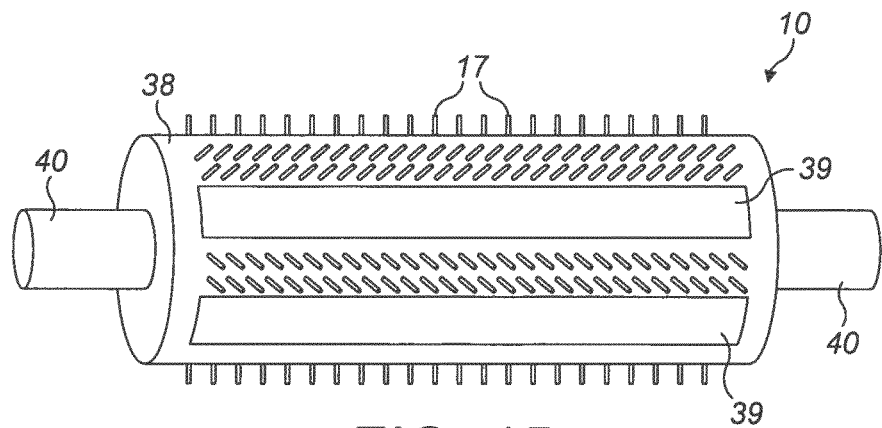
FIG. 15 shows an example of a cold plasma device for treating skin, having a cylindrical manipulator.

In the example of FIG. 15, the manipulator 10 comprises a cylindrical roller 38. The cylindrical roller 38 may comprise a mesh, the cold plasma generator may be located within the mesh. Similarly to the example of FIG. 4a, the mesh itself may be the second electrode of the cold plasma generator.

Alternatively, as shown in FIG. 15, the cylindrical roller 38 may comprise a cylindrical member that includes openings 39, and the cold plasma generator is mounted within the cylindrical roller 38. The openings 39 permit the reactive species of the cold plasma to reach the skin during use of the device.

The cylindrical roller 38 may include a plurality of protrusions 17. The protrusions 17 may be attached to, or integral with, the cylindrical roller 38. The protrusions 17 may be rigid, or they may be resiliently deformable for example made from a rubber material. In some examples, the protrusions 17 may be bristles, or groups of bristles.

The cylindrical roller 38 includes pivots 40 about which it rotates. The cold plasma generator within the cylindrical roller 38 may be electrically connected to a power source via electrical connections in one or more of the pivots 40.

Figure 16:
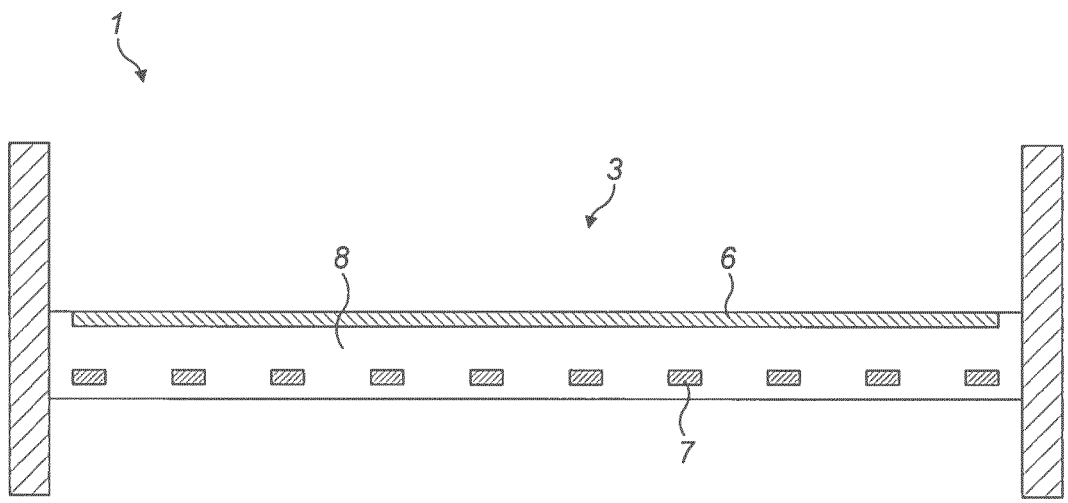
FIG. 16 shows an example cold plasma generator.

FIG. 16 shows an alternative cold plasma generator 3. In this example, the cold plasma generator 3 comprises a first electrode 6 and a second electrode 7 embedded within a dielectric material 8. This arrangement is a self-sterilising surface cold plasma generator, as previously mentioned.

Figure 17:
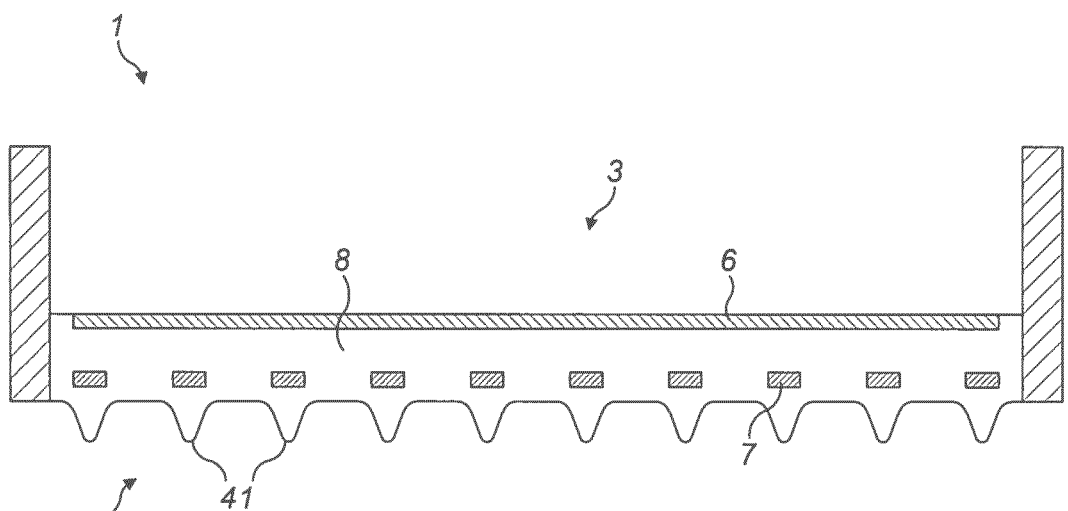
FIG. 17 shows another example cold plasma generator with an integrated manipulator.

FIG. 17 shows an example of a cold plasma device 1 having a self-sterilising surface cold plasma generator 3 and a manipulator 10.

In this example, the surface of the dielectric material 8 that faces the skin during use of the device is profiled, and constitutes the manipulator 10. In particular, as shown in FIG. 17 the dielectric material 8 is provided with a plurality of protrusions 41 that manipulate the skin as the device is used.

The protrusions 41 may be arranged in an array, or in lines. The protrusions 41 may be elongate ridges and extend across the surface of the dielectric material 8, or they may be conically shaped protrusions.

Figure 18:
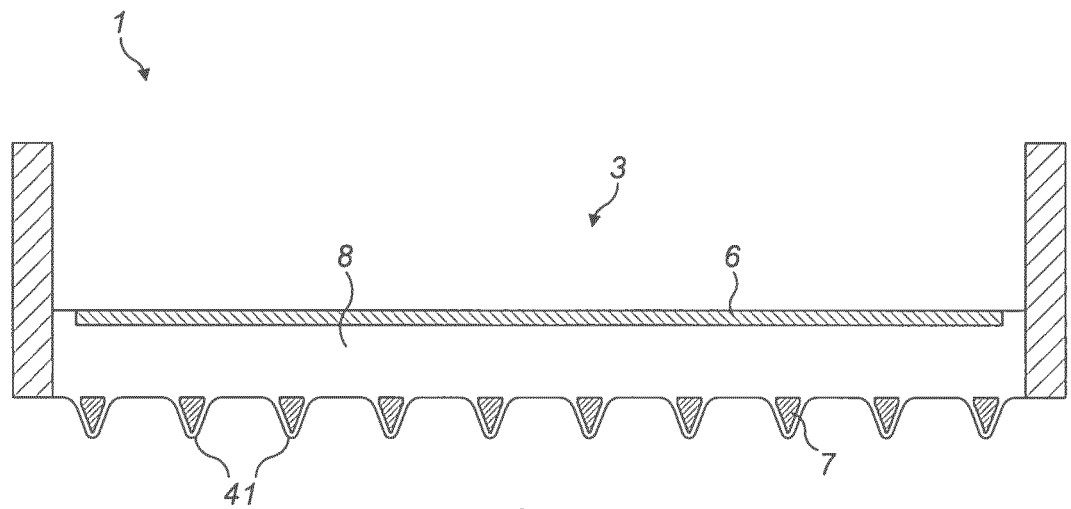
FIG. 18 shows another example cold plasma generator with an integrated manipulator; and, FIG. 19 shows another example cold plasma generator with an integrated manipulator.

FIG. 18 shows an example similar to that of FIG. 17, but the second electrode 7, embedded within the dielectric material 8, is shaped to substantially match the shape of the profiled surface of the dielectric material 8, in particular the protrusions 41.

As shown in FIG. 18, the second electrode 7 is shaped such that there is a substantially even distance between the outer surface of the protrusions 41 and the second electrode 7. Therefore, reactive species are more evenly generated across the cold plasma generator 3.

Figure 19:
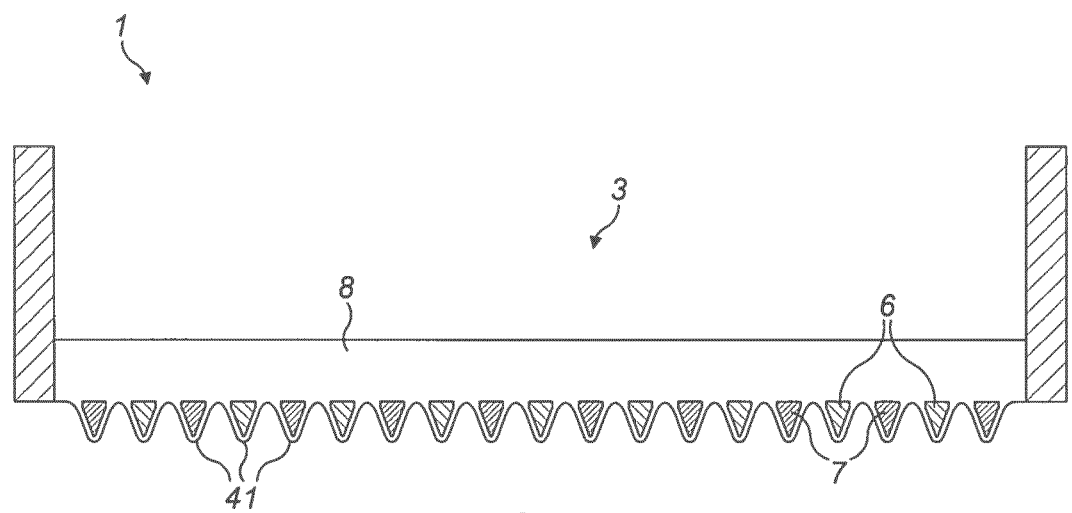

FIG. 19 shows another example similar to those of FIG. 17 and FIG. 18. In this example, the first electrode 6 and the second electrode 7 are arranged such that they are equally spaced from the outer surface of the dielectric material 8. In this example, the first and second electrodes 6, 7, embedded within the dielectric material 8, are interwoven with each other, but always separated by the dielectric material 8. Both the first and second electrodes 6, 7 are shaped to substantially match the shape of the profiled surface of the dielectric material 8, in particular the protrusions 41. This creates a substantially even distance between the outer surface of the protrusions 41 and the first and second electrodes 6, 7. Therefore, reactive species are more evenly generated across the cold plasma generator 3.

The above embodiments as described are only illustrative, and not intended to limit the technique approaches of the present invention. Although the present invention is described in details referring to the preferable embodiments, those skilled in the art will understand that the technique approaches of the present invention can be modified or equally displaced without departing from the spirit and scope of the technique approaches of the present invention, which will also fall into the protective scope of the claims of the present invention. In the claims, the word "comprising" does not exclude other elements or steps, and the indefinite article "a" or "an" does not exclude a plurality.

Any reference signs in the claims should not be construed as limiting the scope.

The invention claimed is:

1. A cold plasma device for treating skin, the cold plasma device comprising:
a housing having an end face,
a cold plasma generator adapted to generate cold plasma that produces reactive species for treating said skin, wherein the cold plasma generator is substantially evenly spaced from said skin during use, and a manipulator connected or coupled to the end face of the housing and adapted to manipulate said skin to increase exposure of bacteria on said skin to said reactive species during use of the device, wherein said manipulator extends between the cold plasma generator and the said skin during use; wherein the manipulator comprises a movable member movable relative to the manipulator, said movable member arranged to contact said skin to be treated during use of the cold plasma device.

2. The cold plasma device of claim 1, further comprising an actuator adapted to move the movable member relative to the remainder of the cold plasma device.

3. The cold plasma device of claim 1, wherein the manipulator comprises a stretcher member.

4. The cold plasma device of claim 3, wherein the stretcher member is pivotally mounted to the cold plasma device.

5. The cold plasma device of claim 3, wherein the manipulator comprises a plurality of stretcher members arranged in adjacent lines.

6. The cold plasma device of claim 5, wherein a distance between the plurality of stretcher members are greater than a length of the stretcher members.

7. The cold plasma device of claim 3, further comprising an actuator adapted to rotate the stretcher member.

8. The cold plasma device of claim 1, wherein the manipulator is cylindrical and is adapted to be rolled across said skin.

9. The cold plasma device of claim 1, wherein the manipulator is spherical and is adapted to be rolled across said skin.

10. The cold plasma device according to claim 1, wherein the manipulator comprises a fixed member arranged to contact said skin during use of the device.

11. The cold plasma device of claim 1, wherein the manipulator comprises a mesh.

12. The cold plasma device of claim 1, wherein the manipulator comprises a plurality of protrusions adapted to contact said skin during use of the cold plasma device.

13. The cold plasma device of claim 1, wherein the manipulator comprises a resiliently flexible material, and the manipulator is adapted to the shape of the skin being treated.

14. The cold plasma device of claim 1, wherein the cold plasma generator and the manipulator are integrally formed, with the manipulator being disposed on a surface of the cold plasma generator.

15. The cold plasma device of claim 1, wherein the manipulator is configured to smooth out wrinkles.

16. The cold plasma device of claim 1, further comprising an actuator adapted to cause the movable member to vibrate relative to the device.

17. The cold plasma device of claim 1, further comprising a belt adapted to contact the skin, wherein the belt is mounted on at least two rollers, wherein an actuator is adapted to rotate the belt.

18. The cold plasma device of claim 1, wherein the cold plasma generator comprises a first electrode and a second electrode that are embedded within a dielectric material, wherein a surface of the dielectric material comprises the manipulator.

19. The cold plasma device of claim 18, wherein the second electrode comprises openings configured to permit reactive species of cold plasma filaments to reach the skin during use of the device.

20. The cold plasma device of claim 1, wherein the manipulator comprises a ring-shaped plate, the plate comprising a plurality of protrusions.

* * * * *